United States Patent [19]

Linet

[11] 4,150,089

[45] Apr. 17, 1979

[54] MULTI-CHAMBER TEST TUBE

[76] Inventor: Michael S. Linet, 8213 SW. 72 Ave., Miami, Fla. 33143

[21] Appl. No.: 830,415

[22] Filed: Sep. 6, 1977

[51] Int. Cl.² ............................................. A61M 5/00
[52] U.S. Cl. .................................... 422/102; 128/2 F; 128/2 G; 128/297; 128/350 V; 128/DIG. 5; 422/103; 215/6
[58] Field of Search .................. 23/292; 128/2 F, 2 G, 128/DIG. 5, 276, 297, 215, 350 V; 215/6

[56] References Cited

U.S. PATENT DOCUMENTS

| 2,720,307 | 10/1955 | Morgan | 215/6 X |
|---|---|---|---|
| 3,405,706 | 10/1968 | Cinqualbre | 128/DIG. 5 |
| 3,446,342 | 5/1969 | Michel | 206/232 |
| 3,494,351 | 2/1970 | Horn | 128/2 F |
| 3,604,410 | 9/1971 | Whitacre | 128/2 F |
| 3,848,579 | 11/1974 | Willa-Real | 128/2 F |
| 3,874,367 | 4/1975 | Ayres | 128/DIG. 5 X |

FOREIGN PATENT DOCUMENTS

| 562747 | 12/1957 | Belgium | 215/6 |
|---|---|---|---|
| 366638 | 6/1923 | Fed. Rep. of Germany | 215/6 |
| 1208412 | 10/1970 | United Kingdom | 128/2 F |

Primary Examiner—Joseph Scovronek
Assistant Examiner—Arnold Turk

[57] ABSTRACT

A multi-chamber test tube which includes a first and a second matched separate elongate tubular member, means to connect the members together defining a test tube means having a dual mouth, and a stopper having a first leg and a second leg extending from the stopper body and receivable within the first and second elongate tubular member and wherein a pathway is provided from a central cavity in the body of the stopper through each of the legs and wherein a one-way valve is provided in each of the leg paths which is normally closed yet yieldable to permit flow through the leg paths in response to an elevated pressure in the cavity relative to the interior of the test tube.

9 Claims, 5 Drawing Figures

MULTI-CHAMBER TEST TUBE

FIELD OF THE INVENTION

This invention relates to a blood collection test tube and, more particularly, to a blood collection test tube composed of interconnected separable and separate tube segments which are joined together for purposes of taking the sample and which are separated for conducting tests.

BACKGROUND OF THE INVENTION

As is explained in some detail in U.S. Pat. No. 3,604,410, at column 1, at about line 40, in many cases, there is a need for multiple blood samples and this has given rise as technology has advanced to this stage, to problems with equipment which have, in the past, been satisfactory when only one sample was necessary, all as is explained in some detail in column 1 of the above referenced patent at about line 32 wherein blood is caused to discharge creating a general mess, soiling clothing, etc. In the early stages, when the need was first realized, an earlier prior art patent is represented by that granted to Horn, U.S. Pat. No. 3,494,351 which comprises a relatively bulky device wherein a plurality of separate test tubes are held by a holder 10 and through which various passageways are provided to conduct a flow of blood into the several test tubes. This, however, is a frightening thing to connect to a patient and in some hospitals might not well be used for fear of scaring the patient to death or at least to the point where it is better to go back to the problems described in the above mentioned U.S. Pat. No. 3,604,410. Another prior art patent illustrating the earlier efforts to resolve the patent is that of U.S. Pat. No. 3,405,706. The above mentioned U.S. Pat. No. 3,604,410 does represent the closest prior art; however, the applicant has presented hereinafter a distinctly different advance in this art in that the applicant's invention is not as cumbersome, is of a different construction, utilizes less number of parts, for example, a plurality of insert needles for insertion into tube stoppers is not required, and, generally, represents a compact and smaller device for attachment, generally in the manner as shown in FIG. 1 of U.S. Pat. No. 3,604,410. In short, applicant's device utilizes a single tube which is separated into separate but separable tube segments which are configured so as to be adapted to be joined together to form a cylindrical test tube means having a test tube configuration. More particularly, it will be seen upon general reference to the drawings that the instant invention is composed of a pair of test tube segments. These segments are joined together in abutting relation along a medial line. Each of the segments has an open upper end. The ends are closed by a single stopper. In order to do this, the stopper has a leg or portion in the upper end of each of the test tube segments. The stopper, above the legs, has a body which is provided with a central internal cavity. A passageway leads downwardly from the cavity through each of the legs opening into one of the test tube segments. In use, the needle of a cannula is inserted through the top of the stopper so that the point is in the cavity. This provides a flow path for blood through the cannula and stopper and into the test tube segments. The blood moves along or through this pathway readily because, as is conventional, the interior of the test tube is evacuated causing a pressure differential. Hence, once the cannula is inserted into the arm and connected to the stopper of the test tube, the blood will move through it and into the test tube. In this manner, two separate specimens are obtained for utilization in tests. It is also described hereinafter, wherein a flap or valve means is provided so that there is no backflow from one of the test tube segments through the pathways in the legs and central cavity to cross over to the other of the test tube segments. There is thus provided two, separate, clean samples. In this manner one may use an anti-coagulent in the testing of one of the blood specimens being obtained and no anti-coagulent or other material in the other of the blood specimens being obtained, all for the purpose of subsequent testing in accordance with well-known procedures in the art.

OBJECTS OF THE INVENTION

It is, accordingly, an object of this invention to provide an improved blood sampler wherein a test tube means is provided which is composed of two or more test tube segments which are companionately shaped to interengage with one another to define a test tube configured means and wherein a stopper is provided which is composed of a lower portion having feet, each of which is adapted to be received in the mouth of the test tube segments to close it and through which a passageway is provided in each leading to a common central cavity which is adapted to be pierced by a needle.

It is another object of this invention to provide an improved stopper of the type described more fully hereinafter. The stopper is improved in that it includes a valve means which is adapted to be used with a plurality of matched or companionate test tube segments which are temporarily joined together in a test tube configuration. This improved stopper is adapted to distribute the blood from a patient evenly into the several test tube segments. The valve means of the stopper is provided so that the several samples are not contaminated one with the other.

It is another object of this invention to provide a blood sample of the type described hereinafter which is relatively simple to construct, inexpensive to use, and which will cause less loss of specimens and, moreover, avoid a problem of the past, to wit, mixing of specimens from different patients. The latter is avoided because the specimens from a given patient may be conveniently kept together until reaching the laboratory where the various samples from a single patient may be separated for the testing procedure.

In accordance with these and other objects which will become apparent hereinafter, the instant invention will now be described with reference to the accompanying drawings in which:

DESCRIPTION OF PREFERRED EMBODIMENT

Figure 1:
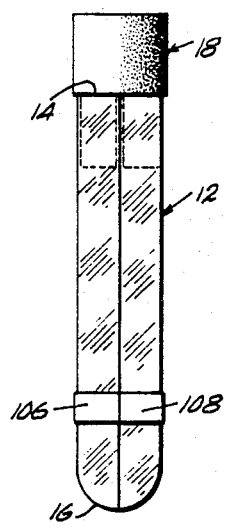
FIG. 1 is an elevation view of the instant invention.

Referring to the drawings wherein like reference characters designate like or corresponding parts throughout the several views the numeral 12 generally designates a test tube means which has an upper end 14 which is open and a lower end 16 which is closed and wherein the upper end is provided with a stopper or cap 18.

Figure 2:
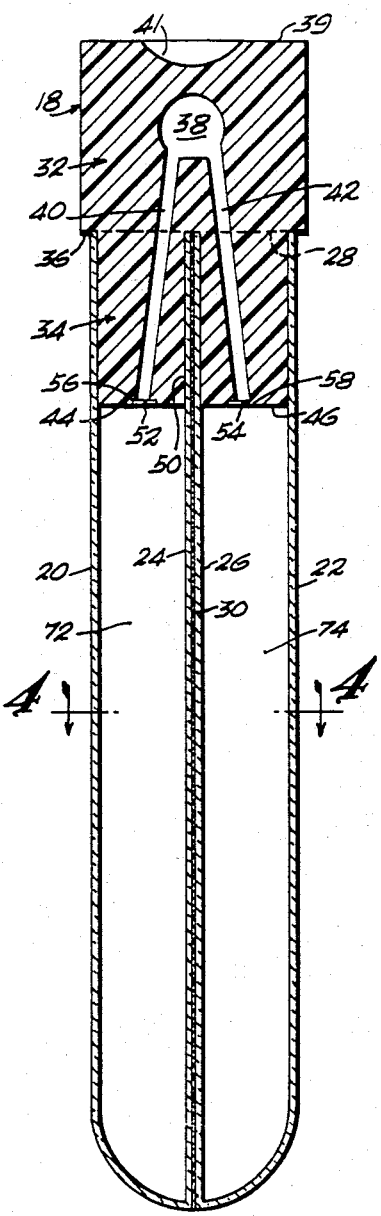
FIG. 2 is an elevation view in cross section of the invention as shown in FIG. 1.
Figure 4:
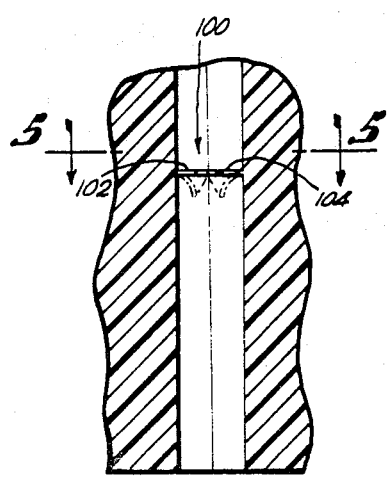
FIG. 4 is a view in cross section of a zone of the invention such as that indicated by the numerals 68 or 70 and illustrating an alternative embodiment of the instant invention in that a different type of valve means is utilized other than that shown in FIGS. 2 and 3 and designated by the numerals 52 and 54.

Referring now to FIG. 2, it is seen that the test tube means generally designated by the numeral 12 comprises a multi-chambered test tube means and that it may be composed of a first and a second test tube segment 20 and 22 and wherein each of these test tube segments includes a side wall means such as 24 and 26 which are in abutting engagement with one another with their respective upper ends being arranged in a plane such as at 28 and wherein adhesive means 30 are provided so that the abutting surfaces remained joined together but releasable, such as by an adhesive and which, when in abutting relation define a cylindrical test tube means of circular cross section, see FIG. 4. While shown in the form of two test tube segments, it will be understood that two, three, or indeed, four test tube segments may be utilized; however, within the concept of this invention the preferred embodiment is shown with two generally semi-circular test tubes as seen in cross section.

With respect to the cap or stopper 18, it is seen that it is composed of an upper portion 32 and a lower portion 34 with a shoulder, the latter being of a somewhat reduced diameter defining a shoulder 36 therebetween or the stop means, as will be explained more fully hereinafter which is in the plane indicated by the numeral 28. The upper portion 32 is provided with a central cavity 38 about midway of the distance between the upper surface 39 and the shoulder 36 and which is centrally or axially arranged as shown. From the central cavity there extends downwardly a bifurcated passageway providing a first path 40 and a second path 42, each of which terminate at the lower end 44 and 46 of the lower portion 34 and at which there is provided a valve means 52 and 54 normally closing the passageway and wherein the valve means comprises the flaps shown which are hingedly connected to the lower portion 56 and 58. In the upper portion top surface 39 as is standard in the industry and as is well known there is a dish-shaped recess 41 which is for the purpose of guiding a needle which is utilized to introduce blood into the test tube means and, in the embodiment shown is utilized to guide a needle into the cavity 38.

The use of the unit will now be explained on reference to FIG. 3. It will be noted that the lower portion 34 of the stopper 18 is provided with a diammetrical slit 50 so that the lower portion is composed of two feet, each of which is sized to be received in the respective mouths of the test tube segments 20 and 22 and inserted until the shoulder 36 dwells upon the upper end 14 of the test tube means 12.

Figure 3:
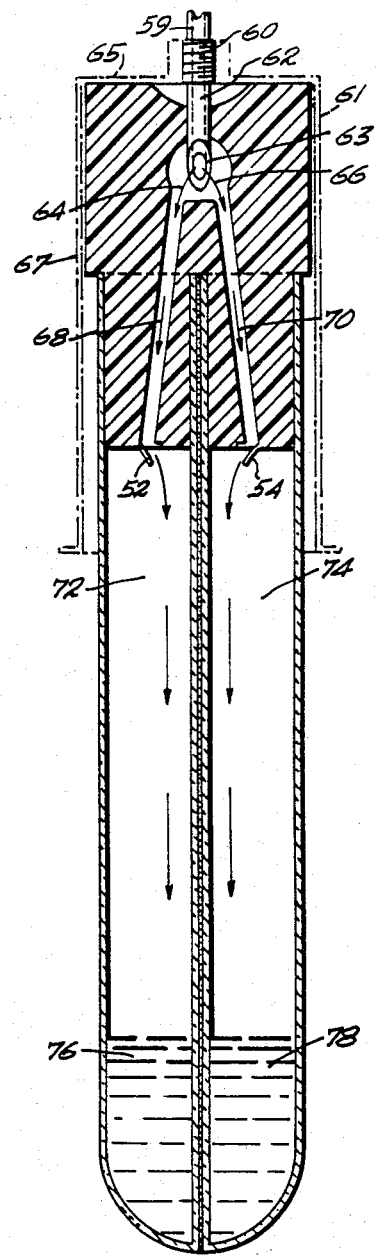
FIG. 3 is a view similar to FIG. 2 and illustrating the use of the instant invention.

With reference to FIG. 3, the utilization of the test tube means will now be explained. Conventionally, a cannula generally designated by the numeral 59 is inserted into the vein of a patient and the cannula is provided with a holder 61 between the inserted end, not shown, of the cannula 59 and a distribution end 63. In a conventional prior art embodiment the holder 61 provides a hood-shaped member sized to receive the test tube means and which provides a roof 65 and side walls or a skirt 67 which guides the entry of the test tube means in relation to the insert needle 63 and, in combination with the thickness of the upper portion determines the penetration of the needle. While the holder does not comprise the invention, it is referred to here for purposes of illustration and in order to understand the use of the instant invention.

Once the test tube means together with the stopper has been inserted into the holder, and the upper surface 39 is in engagement with the roof 65 of the holder the needle will be inserted as shown at 63 to the proper depth and in the cavity 38. Customarily the interior of the test tube means is evacuated as is the practice in the field. This results in the following: blood will be drawn by the differential inpressure along the arrowed lines indicated in FIG. 3 filling the compartments 72 and 74 proceeding along the arrowed lines 64 and 66, 68 and 70 and as indicated by the lines 76 and 78 indicating blood which has been drawn into the tubes.

Referring to the stopper 18, it is preferably composed of two portions which are symmetrical with respect to a diammetrical plane and composed of two portions which are fused together along the plane which appears in FIG. 2. Additionally, as shown in FIG. 1 indicator tapes or suitable means such as 106 and 108 may be utilized for the purpose of color-coding the tubes for future reference in connection with the testing procedures, as is standard in the industry.

Figure 5:
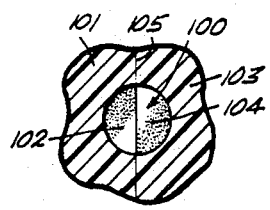
FIG. 5 is a view in cross section taken on the plane indicated by the line 5—5 of FIG. 4 and looking in the direction of the arrows.

Referring now to FIGS. 4 and 5, an alternative type of flap means is shown. In this embodiment, the valve means or flap means comprise semi-circular or relatively thin shelves which extend outwardly as shown in FIG. 5 and are indicated by the numerals 102 and 104 of the valve 100 and which meet at the midline of the fused portions 101 and 103 in accordance with the construction described in the preceding paragraph. It will be seen that these shelves or flaps are of relatively thin thickness, see FIG. 4, so that, under the influence of the differential inpressure encountered in the both described procedures, they will be deformed slightly, as is exaggerated in FIG. 4, permitting blood to pass between the flaps along the midline 105 and into the tubes. One of these flap means will be provided in the alternative embodiment intermediate the length of each of the legs at any suitable location along the lengths thereof between the cavity and the entrance or the surfaces 44 and 46.

The material of the stopper is of conventional medical grade rubbery material and the test tube means segments are of glass. Any suitable bonding adhesive for uniting the segments together may be utilized, such as that which is currently on the market and sold under the trademark 3M Company Adhesive which is rubbery and can be peeled away to separate the segments readily. The color coding may be accomplished by painting, or, as is currently being utilized, a plastic colored surface coating. The legs of the stopper may be color coded and the coding may be throughout the entire relevant half of the entire stopper body.

While the preferred embodiment has been described hereinbefore, it is within the scope and spirit of this invention to provide a somewhat modified construction for the stopper, including, but not limited to, a pair of segments which are united along a central plane perpendicular to the plane illustrated in FIGS. 2 and 3; and wherein the stoppers are separable. Additionally, while the test tube segments have been, for the most part, described herein as being a pair of segments, it will be recognized that within the spirit and scope of this invention a plurality of test tube segments which are matched and adapted to mate to form the test tube means may be utilized and, in that event, a companionately shaped multi-legged stopper will be provided, all to the end that more than two test specimens may be collected. In the event that more than two test tube segments are utilized, then, if desired, the stopper may be separable into a component adapted to close the mouth of each of the test tube segments and to be connected together when the test tube segments are in test tube defining relation with respect to one another to form a common stopper for the unit. While the color coding described may be applied exteriorly as shown, other techniques may be utilized for color coding the test tube segments, such as interior or exterior color coding techniques. It will further be recognized that while the preferred material according to present technology for the test tube is an inert material such as glass, there may be other types of materials utilized within the scope of this invention and, further, while the stopper is of a suitable type of rubbery material, such as surgical rubber, other types of stopper material may be employed.

What is claimed is:

1. A multi-chambered test tube means of circular cross section comprising:

first and second matched separate elongate tubular members of rigid material, each of said members having an open end and elongate side wall means, said side wall means of each said member having a zone adapted for abutting relation;

means to hold the tubular members together in abutting relation thereby defining a cylindrical test tube means of circular cross section, said members being of a common length and their respective open ends being in a common plane defining a mouth of the test tube means, when the tubular members are in abutting relation;

said normally abutting zones of said side wall means of said members defining a septum of said tube means;

a stopper for said test tube means, said stopper having a body with a first and a second end, said first end having a slit extending depthwise toward the second end and said slit being sized and located to receive the septum, said slit separating the body adjacent the first end into a first and a second leg, said legs being sized for snug nesting in the open first and second ends respectively of said tubular members, the body of said stopper adjacent the second end having a diameter larger than the diameter of said first end defining a shoulder to dwell on the open end of the tube means when the legs are in the open ends of said tubular members to limit penetration of said stopper into said tubular member;

a central cavity in the stopper body between the ends and intermediate the slit and the second end, and a bifurcated passageway with a first leg path extending from the cavity through the first leg and to the first end of the stopper and a second leg path extending from the cavity through the second leg and to the first end of the stopper;

one-way valve means in each of the leg paths and normally closed and yieldable to permit flow through the leg paths in response to an elevated pressure in the cavity relative to the interior of the tube means.

2. The device as set forth in claim 1 wherein said means to hold the tubular members together comprise adhesive means.

3. The device as set forth in claim 1 wherein the second end of said stopper includes a central dish-shaped recess comprising guide means for guiding a needle to be introduced into the central cavity.

4. The device as set forth in claim 1 wherein the stopper comprises a first and a second portion symmetrical with respect to a diametrical plane passing longitudinally through the stopper and including a surface of abutment in each portion and each of said surfaces of abutment including a portion of said central cavity and said bifurcated legs.

5. The device as set forth in claim 1 including indicator tapes on the exterior surface of said tubular members comprising color coding means for the tubes for reference in connection with testing procedures.

6. The device as set forth in claim 1 wherein said one-way valve means in each of the leg paths comprises a flap means in each leg path having a first normal position spanning the associated leg path and yieldable in a direction of swinging movement away from said second end of said stopper.

7. The device as set forth in claim 6 wherein said flap means are disposed at said first end of said stopper means.

8. The device as set forth in claim 6 wherein the flap means are disposed intermediate said first and second end.

9. The device as set forth in claim 1 wherein said stopper is of rubbery material of medical grade.

* * * * *